United States Patent [19]
Eastgate et al.

[11] Patent Number: 5,534,998
[45] Date of Patent: Jul. 9, 1996

[54] SAMPLE NEBULIZER AND EVAPORATION CHAMBER FOR ICP AND MIP EMISSION OR MASS SPECTROMETRY AND SPECTROMETERS COMPRISING THE SAME

[75] Inventors: Alan R. Eastgate, La Praz; Wilfried Vogel, Cully, both of Switzerland

[73] Assignee: Fisons PLC, Ipswich, England

[21] Appl. No.: 290,822

[22] Filed: Dec. 14, 1994

[30] Foreign Application Priority Data

Feb. 19, 1992 [GB] United Kingdom ............... 9203463

[51] Int. Cl.$^6$ ............... G01N 1/00; G01N 21/73; H01J 49/04
[52] U.S. Cl. ............... 356/316; 356/36; 250/288
[58] Field of Search ............... 356/315, 316, 356/311, 36; 250/288

[56] References Cited

U.S. PATENT DOCUMENTS 3,438,711  4/1969  Hell ............... 356/315

FOREIGN PATENT DOCUMENTS 2356927    1/1978  France .
3233130    3/1984  Germany .
3330424    3/1985  Germany .
WO/9202282 2/1992  WIPO .

OTHER PUBLICATIONS

Blakley et al, Journal of Chromatography, vol. 158, 1978 pp. 261–276.

Goulden et al, Analytical Chemistry, vol. 56, No. 3, Nov. 1984, pp. 2327–2329.

Primary Examiner—F. L. Evans
Attorney, Agent, or Firm—Chilton, Alix & Van Kirk

[57] ABSTRACT

The invention provides a nebulizer and spray chamber (3) for producing an aerosol (7) suitable for feeding into the plasma torch of an ICP or MIP emission or mass spectrometer. The aerosol (7) is subjected to rapid radiative heating (26) to evaporate the smaller droplets to dryness and preferably to cause the larger droplets to disintegrate into smaller droplets before they are completely evaporated. Nebulizer/spray chamber combinations according to the invention have higher sample transport efficiency than prior types. Optical and mass ICP and MIP spectrometers incorporating the nebulizer and spray chamber are also disclosed.

30 Claims, 5 Drawing Sheets

SAMPLE NEBULIZER AND EVAPORATION CHAMBER FOR ICP AND MIP EMISSION OR MASS SPECTROMETRY AND SPECTROMETERS COMPRISING THE SAME

This invention relates to a sample nebulizing and evaporation chamber device for producing from an analyte contained in a liquid an aerosol which may be fed to the plasma torch of an inductively-coupled plasma (ICP) or microwave-induced plasma (MIP) optical or mass spectrometer.

Liquid samples comprising an analyte are conventionally introduced into the torch of an ICP or MIP spectrometer by means of a nebulizer which produces an aerosol of the liquid in an inert gas such as argon. Suitable concentric and cross-flow pneumatic nebulizers, ultrasonic nebulizers and thermospray nebulizers are described and compared by Sharp in J. Analytical and Atomic Spectrometry, 1988 vol 3 pp 613–652. Prior nebulizers typically produced aerosols which comprise droplets with diameters much greater than the optimum of less than 10 micron which is required for the plasma torch, so that it is conventional for the nebulizer to discharge into a spray chamber whose primary function is to remove the large droplets and which may also cause at least some desolvation of the smaller droplets. The design of spray chambers is discussed by Sharp in J. Analytical Atomic Spectrometry, 1988, vol 3 pp 939–963.

In a spray chamber, large droplets may be removed by inertial deposition which is a consequence of the pattern of flow in the chamber. The effect may be enhanced by causing the aerosol to impinge on a physical obstruction in its path or by otherwise causing the gas flow to abruptly change direction. However, this process results in loss of the analyte contained in the large droplets. Smaller droplets traversing the chamber may undergo evaporative loss and some will typically be evaporated to dryness. In prior nebulizer—spray chamber devices the process of droplet evaporation may be enhanced by heating the liquid prior to nebulization, by cooling the walls of the spray chamber, and by the use of a secondary condenser through which the aerosol passes after it has left the spray chamber. However, because the evaporation of liquid from droplets greater than 1 or 2 microns in diameter is quite slow in comparison with the typical residence time in the spray chamber, the desolvation obtained in prior spray chambers is far from complete.

Spray chambers having heated walls are disclosed by Thompson and Walsh in "A Handbook of ICP Spectrometry", published by Blackie, 1983, at p 69. These are unsatisfactory because of cross-contamination problems resulting from a build-up of analyte on the spray chamber walls.

Thermospray nebulizers (eg, the liquid chromatography—mass spectrometry interface described by Vestal and Fergusson in Analytical Chemistry, 1985 vol 13 pp 2373–8) are an extreme case of a nebulizer system incorporating solvent heating. In thermospray nebulizers the liquid sample is pumped through a strongly heated capillary tube so that vaporization of the solvent takes place in it and an aerosol-vapour mixture emerges at high velocity from the end of the tube.

An earlier version of the thermospray nebulizer (Blakely, McAdams, Vestal, J. Chromatog. 1978 vol 158 pp 261–276) comprises a laser which vaporizes a continuous stream of liquid ejected from a capillary in a very short time. However, only the heated capillary version has been adopted for use with an ICP torch (for example, Koropchak and Winn, Anal. Chem. 1986, vol 58 pp 2558–61).

Nebulizer-spray chamber combinations are notoriously inefficient and typically in prior devices less than 5% of the analyte in a liquid is transferred to the torch. It is the object of the present invention to provide a nebulizer-evaporation chamber arrangement for an ICP or MIP torch which exhibits fewer memory effects and is more efficient than prior types, It is a further object to provide optical emission and mass spectrometers comprising such nebulizer-evaporation chamber arrangements.

According to the invention there is provided an apparatus for producing an aerosol of desolvated analyte particles comprising nebulizing means for producing droplets of a carrier liquid containing an analyte, evaporation chamber means, bounded by a wall, for receiving said aerosol, means for subjecting the droplets comprised in said aerosol in said evaporation chamber to rapid radiative heating to evaporate said carrier liquid from said droplets during their passage through said evaporation chamber, and cooling means for maintaining the temperature of said wall below the boiling point of said carrier liquid at the pressure inside said evaporation chamber.

By carrier liquid is meant any sample for analysis in which the analyte(s) are present in a liquid, for example, solutions, slurries, dispersions, suspensions and colloids.

The nebulizer means of the invention may comprise any of the types conventionally used for ICP or MIP spectrometry, ie, concentric or cross-flow pneumatic nebulizers, ultrasonic or thermospray nebulizers, or the special types known as MAK, Meinhard or Babington nebulizers. Conveniently a Meinhard nebulizer may be used for aqueous carrier liquids at flow rates between 0.1 and 10.0 ml/min, or preferably between 0.6 and 3.0 ml/min, with an inert gas (argon) flow rate between 0.1 and 10.0 liters/min, or preferably between 0.4 and 1.0 liters/min. The mean volume diameter of droplets produced by a nebulizer suitable for use in the invention should be less than 50 microns and preferably less than 10 microns.

By rapid radiative heating is meant radiative heating of the sample to a temperature above the boiling point of the liquid carrier within a very short time, say between 0.1 mS and 0.2 S, preferably less than 0.1 S and more preferably less than 50 mS. in order to produce the aerosol of desolvated analyte particles, the rapid radiative heating transfers sufficient heat by radiation to the droplets of the aerosol during their passage through the evaporation chamber to ensure substantially complete evaporation of the liquid from the droplets.

The heating may be achieved by focusing infra-red radiation from a heated body onto the droplets of the aerosol. Preferably the wall of the evaporation chamber is at least in part transparent to the radiation and the heated body is disposed outside the evaporation chamber. The temperature and material of the heated body should be selected to ensure that the frequency of the radiation is such that the droplets will absorb the energy and become heated. A cylindrical elliptical reflector may be used to focus radiant energy from the heated body disposed at one of its foci on to the evaporation chamber disposed at the other.

Preferably the heated body is elongated and disposed at the reflector focus in such a way that its image formed at the other focus is coincident with the path of the aerosol droplets in the evaporation chamber for as long a distance as possible.

A suitable heated body for use with aqueous liquids may comprise an elongate heating element made of silicon carbide and maintained at about 1350° C. by the passage of an electrical current through it. Ideally the heated body should approximate to the classical "black body" radiator of thermodynamics, and any heater which does so would be suitable. The temperature of 1350° C. is chosen to produce radiation which is strongly absorbed by aqueous liquids, but other temperatures can be used for other liquids. The temperature of the heated body may be controlled by a conventional temperature control loop with a sensor such as a thermocouple disposed in the evaporation chamber to receive the reflected radiation.

Alternatively, the aerosol droplets can be heated by microwave energy, for example by disposing the evaporation chamber in a tuned cavity fed from a microwave power generator. The frequency of operation should be selected to coincide with strong adsorption frequencies of the liquid. For aqueous liquids the strongest absorption takes place at 22.3 GHz, but in view of the difficulty in generating sufficient power at this frequency, lower frequencies may be used.

The power of the radiative heating system should be great enough to evaporate substantially all of the liquid from the droplets during their passage through the evaporation chamber, that is, in less than 200 mS and most preferably in less than 50 mS with the inert gas and liquid flow rate ranges suggested above. Ideally, where the liquid is aqueous, droplets of less than 10 microns in diameter should be evaporated to dryness in 10 mS or less. Under the conditions specified, the aerosol at the exit of the evaporation chamber may comprise substantially dry analyte particles of about 1 micron diameter entrained in argon carrier gas at about 120° C.

In a preferred embodiment, condenser means are disposed between the exit of the evaporation chamber and the ICP torch to condense and remove the liquid which has been vaporized in the evaporation chamber. Conveniently the condenser means may comprise a tortuous passage formed in a block of inert material (such as PTFE) sandwiched between two water-cooled plates. Further preferably, a second condenser of similar construction but maintained at approximately 0° C. may be additionally provided between the exit of the first condenser and the plasma torch.

The cooling means may comprise any suitable means for maintaining the wall of the evaporation chamber at a temperature below the boiling point of the liquid. To minimize the radiative heating of the wall, the wall itself should be made of a material transparent to radiation at least at some of the frequencies at which the liquid absorbs energy, and a filter made of a material having the same or similar absorption characteristics as the wall material may be disposed in the path of the radiation from the source to the evaporation chamber. The filter absorbs radiant energy which would otherwise cause heating of the wall of the evaporation chamber. Additional cooling of the evaporation chamber wall, for example by means of a fan, may also be provided to remove heat imparted to it by the condensing liquid. Preferably the evaporation chamber wall is mounted on a water-cooled heat sink to further minimize its temperature rise. When used in conjunction with the heating arrangement described above, the evaporation chamber wall and the filter may be advantageously made from infra-red transmissive quartz. Maintaining the temperature of the wall below the boiling point of the liquid results in the condensation of the liquid on the wall, and this provides a continuous self-cleaning action which minimizes cross-contamination problems.

Although the evaporation chamber may be a flow-through tube it preferably comprises a tube disposed along an axis slightly inclined (20°–30°) to the vertical with the aerosol inlet and outlets in the base of the tube. A drain is provided at the lowest point of the base.

In a most preferred embodiment the radiated heat supplied to the droplets is high enough to cause at least some of them to "explode", ie, be physically disrupted into smaller droplets before they are completely evaporated. Each of the smaller droplets so formed will contain a proportion of the analyte originally contained in the larger droplet, and will be subsequently evaporated to dryness before leaving the evaporation chamber. In this way the substantially dry analyte particles in the gas leaving the evaporation chamber will be smaller than they would have been if the larger droplet had been evaporated to dryness without disruption, and this is highly advantageous in respect of the sensitivity of the spectrometer. This disruption of the droplets does not occur in the prior heated spray chamber design shown by Thompson and Walsh (ibid) because the heat input to the droplets when the wall temperature is 200° C. is too low, so that the larger droplets do not evaporate significantly and are lost from the aerosol by inertial deposition in the chamber.

The invention further provides complete ICP and MIP optical and mass spectrometers in which the prior nebulizer and spray chambers are replaced by the apparatus disclosed above. This portion of the spectrometer in prior instruments is typically responsible for the loss of about 95% of the available sample, while in a spectrometer according to the invention the loss may be reduced to only 50%, leading to a very marked improvement in spectrometer performance.

The invention further provides a method of producing an aerosol comprising small particles of an analyte in a flow of inert gas for an ICP or MIP torch, said method comprising the steps of:

a) nebulizing a liquid containing said analyte to produce an aerosol comprising droplets of said liquid entrained in said flow of inert gas;

b) passing the droplets into a chamber and rapidly heating the droplets comprised in said aerosol by radiant energy to evaporate substantially all the liquid therefrom, thereby producing said aerosol comprising small particles, and c) cooling the walls of the chamber such that the vapour produced by evaporation of said liquid in step b) is condensed and removed from said aerosol.

In a further preferred method the invention provides sufficient heat in step b) for at least some of the droplets present in the aerosol produced by the nebulizer to be disrupted into smaller droplets, each containing a proportion of the analyte originally contained in the droplet prior to its disruption, before all the liquid is completely evaporated from the droplets.

In still further preferred methods the invention provides a method of analyzing an analyte in a liquid by ICP or MIP optical or mass spectrometry wherein said liquid is converted to an aerosol by the method disclosed above and the aerosol so produced is conveyed to the plasma torch of an ICP or MIP spectrometer.

A preferred embodiment of the invention will now be described by reference to the figures, in which.

Figure 1:
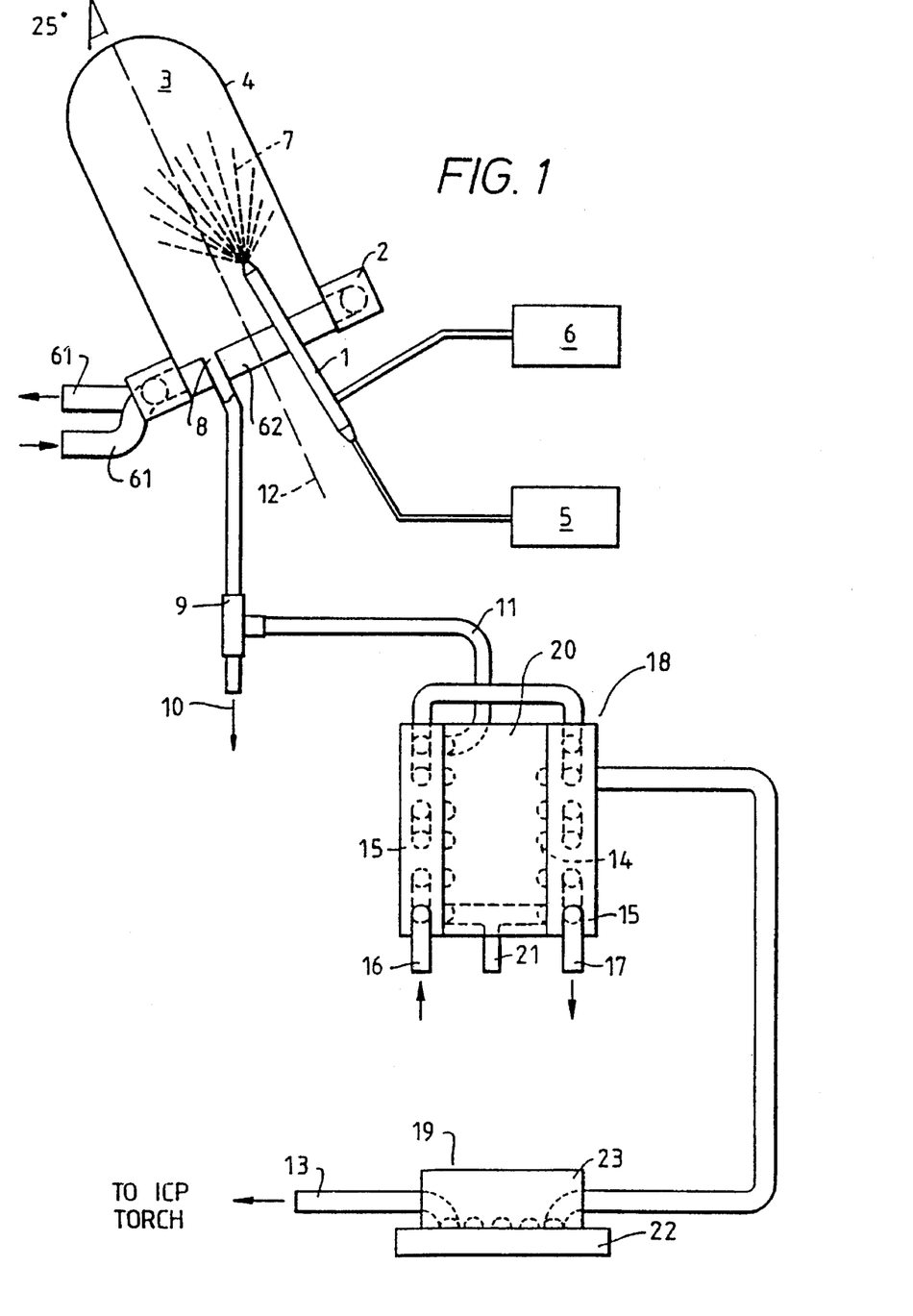
FIG. 1 is a drawing of a nebulizer and spray chamber suitable for use in the invention.

Referring first to FIG. 1 a conventional concentric flow pneumatic nebulizer 1 of the Meinhard type is fitted through a baseplate 2 of an evaporation chamber 3 which comprises a wall 4 of infra-red transmissive quartz. Liquid containing an analyte is delivered to the nebulizer 1 by a liquid delivery system 5 at a flow rate between 0.6 and 3.0 ml/minute, (assuming an aqueous liquid). Inert gas (argon) is fed from a gas supply system 6 into the nebulizer 1 at a flow rate between 0.4 and 1.0 liters/minute. The nebulizer 1 and its associated liquid and gas supply systems 5 and 6 co-operate as in prior ICP nebulizer systems to generate an aerosol of liquid droplets (schematically illustrated at 7 in the figures) in the evaporation chamber 3, each droplet containing a small portion of the analyte.

An outlet 8 is provided in the baseplate 2 and is connected to a T-connection 9 leading to a drain tube 10 through which liquid condensed in the evaporation chamber 3 flows to waste. The longitudinal axis 12 of the chamber 3 is inclined at about 25° to the vertical to ensure that any liquid collecting inside the chamber drains through the outlet 8, T-connection 9 and drain 10. The baseplate 2 comprises a copper heat sink through which cooling water is circulated through the pipes 61 and a base plug 62 of PTFE which closes the bottom of the evaporation chamber 3.

The aerosol generated by nebulizer 1, after the heating process which takes place in the evaporation chamber 3 (described in detail below), leaves via the outlet 8 and T-connector 9 through a tube 11 and passes in turn through a first condenser 18, a second condenser 19, and a pipe 13 which conveys it to the plasma torch. Condenser 18 comprises a block 20 of an inert material such as PTFE on each side of which is cut a tortuous groove 14. The grooves 14 are closed by two water-cooled planes 15 made of aluminium and coated with PTFE on the sides which contact the grooves 14, thereby forming a closed tortuous passage for the aerosol in contact with the cooled surfaces. Cooling water is circulated through passages drilled in the plates through the pipes 16 and 17. A drain 21 is provided at the lowest point of the grooves 14 to allow the escape of any liquid condensed therein. Using cooling water at approximately 15°–20° C. the temperature of the aerosol emerging from the condenser 18 is typically 20°–25° C.

The second condenser 19 is of similar construction to the first condenser 18 but comprises a single cooled plate 22 and a groove cut in one side only of a PTFE block 23. The plate 22 is maintained at approximately 0° C. by means of Peltier effect devices. For convenience the heat sink of these devices may be one of the water-cooled plates 14 or 15 which are comprised in the first condenser 18. The temperature of the plate 22 is electrically regulated by conventional means.

Figure 2:
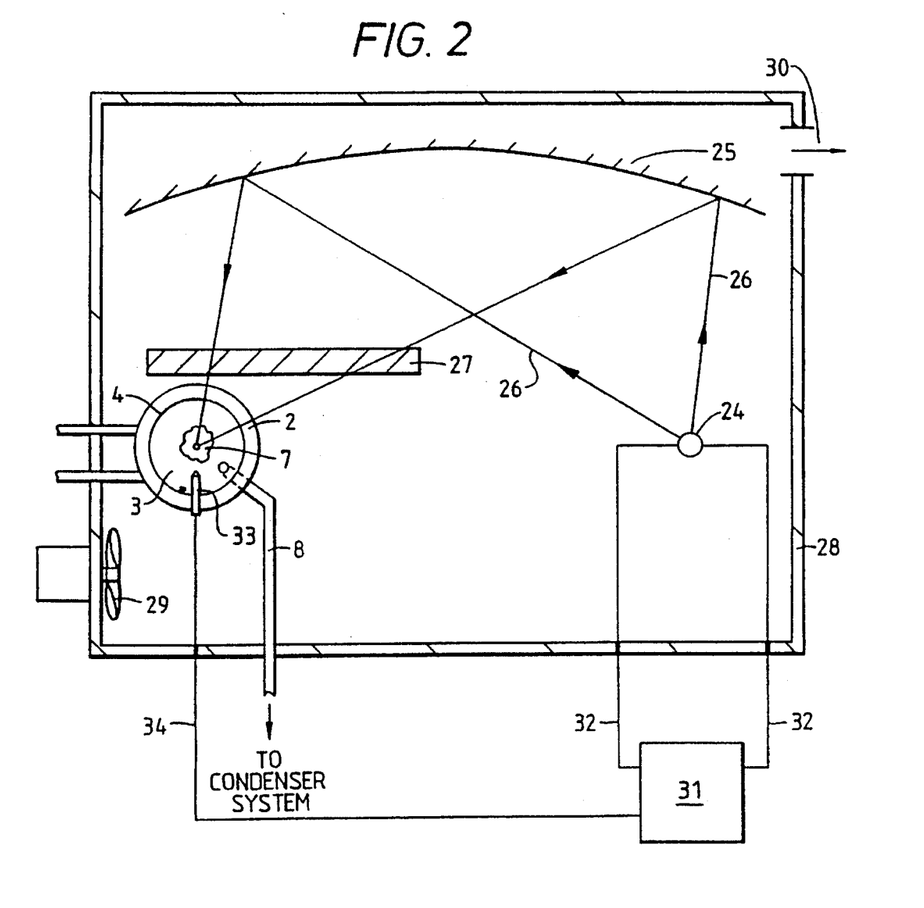
FIG. 2 is a drawing showing how the droplets in the evaporation chamber of the invention may be radiatively heated.

Apparatus suitable for radiatively heating the droplets in the evaporation chamber 3 is shown in FIG. 2. A heated body 24, comprising an elongate silicon carbide heating element, is disposed at one of the foci of a cylindrical elliptical reflector 25 with its longest axis parallel to the axis of the cylindrical reflector. The evaporation chamber 3 is disposed at the other focus of the reflector 25 so that the radiation 26 from the heated body 24 is focused on to the aerosol 7 in the chamber 3 through the quartz wall 4. A filter 27, also made of infra-red transmissive quartz, is disposed between the reflector 25 and the chamber 3 in the path of the radiation 26 to absorb energy at frequencies which would otherwise cause heating of the quartz wall 4 of the evaporation chamber 3. The entire assembly of items 3, 24, 25 and 27 is enclosed in a housing 28 into which cooling air is forced by a fan 29. A vent 30 is provided in the housing 28 for the cooling air to exit. The cooling air is provided primarily to ensure that the temperature of the wall 4 of the evaporation chamber 3 does not exceed the boiling point of the liquid being introduced, but serves also to cool the reflector 25 and the filter 27.

The heated body 24 is maintained at approximately 1350° C. by the passage of an electrical current from a heater power supply 31 via the electrical connections 32. A thermocouple 33, suitably sheathed, is disposed in the evaporation chamber 3 and samples the radiation reflected into the chamber. The thermocouple 33 is connected by leads 34 to the power supply 31 which regulates the power fed to the heated body 24 to ensure that the temperature of the thermocouple 33 remains constant.

Figure 3:
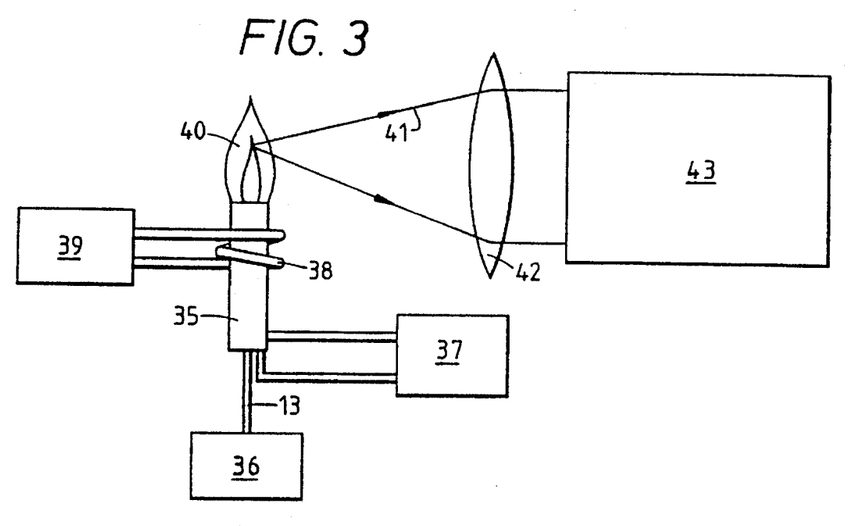
FIGS. 3 and 4 are respectively drawings of ICP optical emission and ICP mass spectrometers according to the invention.

FIG. 3 illustrates schematically an ICP-optical emission spectrometer according to the invention. A conventional ICP plasma torch 35 is fed with the necessary supplies of gas from a gas supply unit 37 and an aerosol generated by a nebulizer system according to FIGS. 1 and 2 identified by the numeral 36 in FIG. 3. The torch 35 is energised by a coil 38 which is fed with RF energy from a power generator 39 so that a plasma flame 40 is formed at the end of the torch. In the flame 40, analyte particles are caused to emit radiation 41 characteristic of their elemental composition which is received by a collection lens 42 and analyzed by a spectrometer 43, as in a conventional ICP emission spectrometer.

Figure 4:
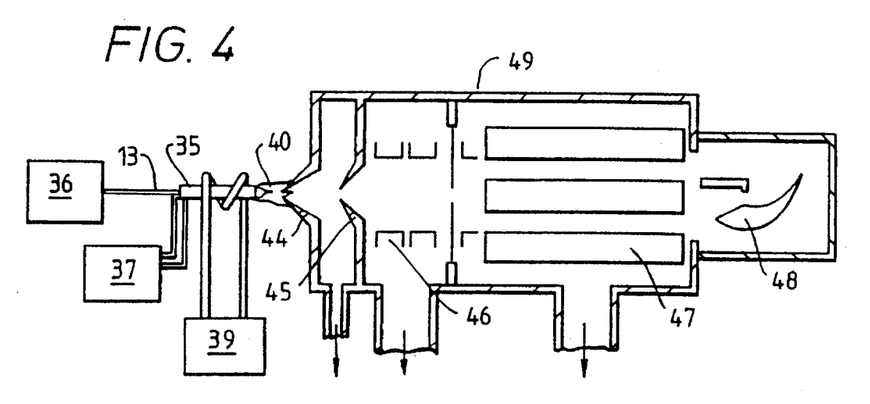

FIG. 4 illustrates schematically an ICP mass spectrometer according to the invention. A plasma flame 40 is generated by items 35–39 as explained for the case of the FIG. 3 embodiment. Ions characteristic of the analyte formed in the flame 40 pass through a small orifice in a sampling cone 44, skimmer cone 45 and ion transfer lenses 46 into a quadrupole mass analyzer 47 and an ion detector 48. Items 44–48 are components of a conventional ICP mass spectrometer generally indicated by the numeral 49.

Figure 5:
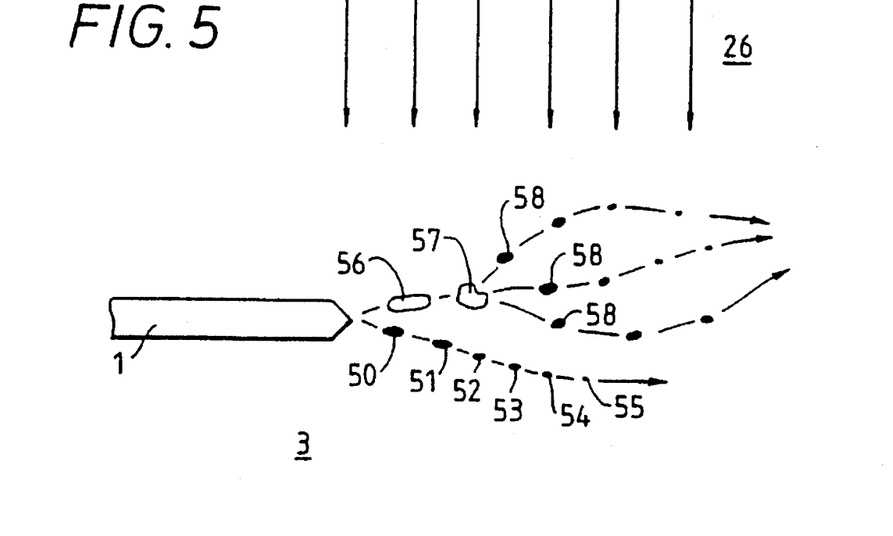
FIG. 5 is a drawing illustrating the behaviour of the aerosol in the evaporation chamber of the invention.

FIG. 5 illustrates the effect of rapid radiative heating on the droplets emerging from the nebulizer 1 in the spray chamber 3. Small droplets for example, droplet 50, in the aerosol 7 will be evaporated to dryness by the radiation 26, as illustrated by the sequence of droplets 50–54, to produce a small particle of analyte 55 which becomes entrained in the gas flow. However, a large droplet for example, droplet 56 will become unstable due to rapid boiling and explode (for example, at 57) to yield several smaller droplets 58 which will subsequently evaporate to dryness (in a similar manner to droplet 50) during their further passage through the radiation 26.

Figure 6:
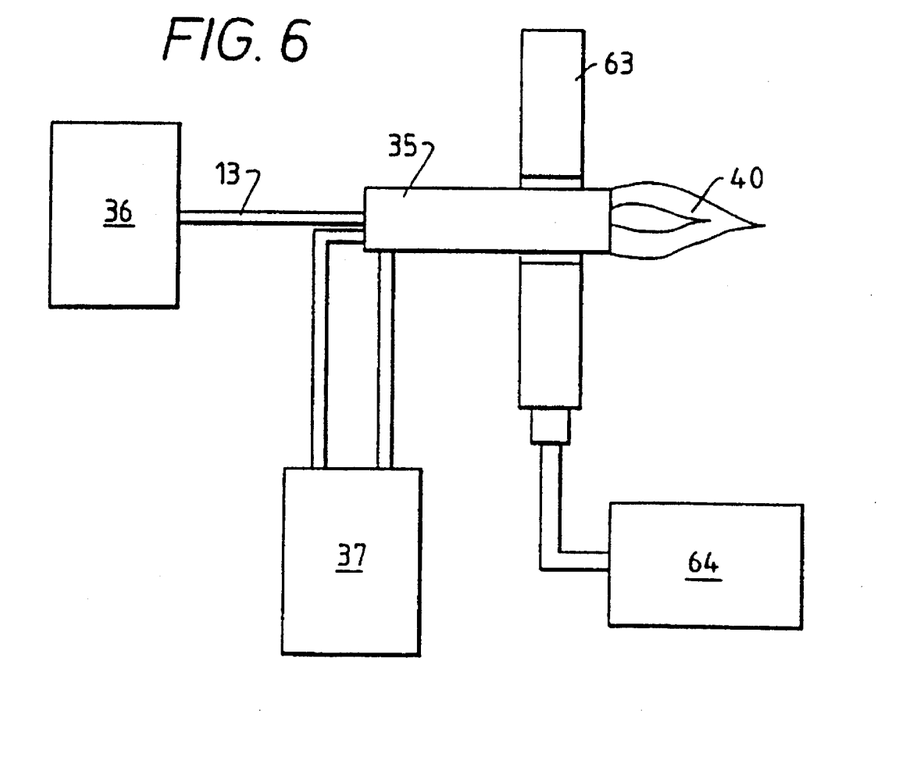
FIG. 6 is a drawing showing how the spectrometers of FIGS. 3 and 4 can be modified for use with an MIP.

The invention also provides MIP optical and emission spectrometers. These are identical to the spectrometers illustrated in FIGS. 3 and 4 except that the coil 38 and the RF power generator 39 may be replaced by a tuned microwave cavity 63 (FIG. 6) fed by a microwave power generator 64.

Figure 7:
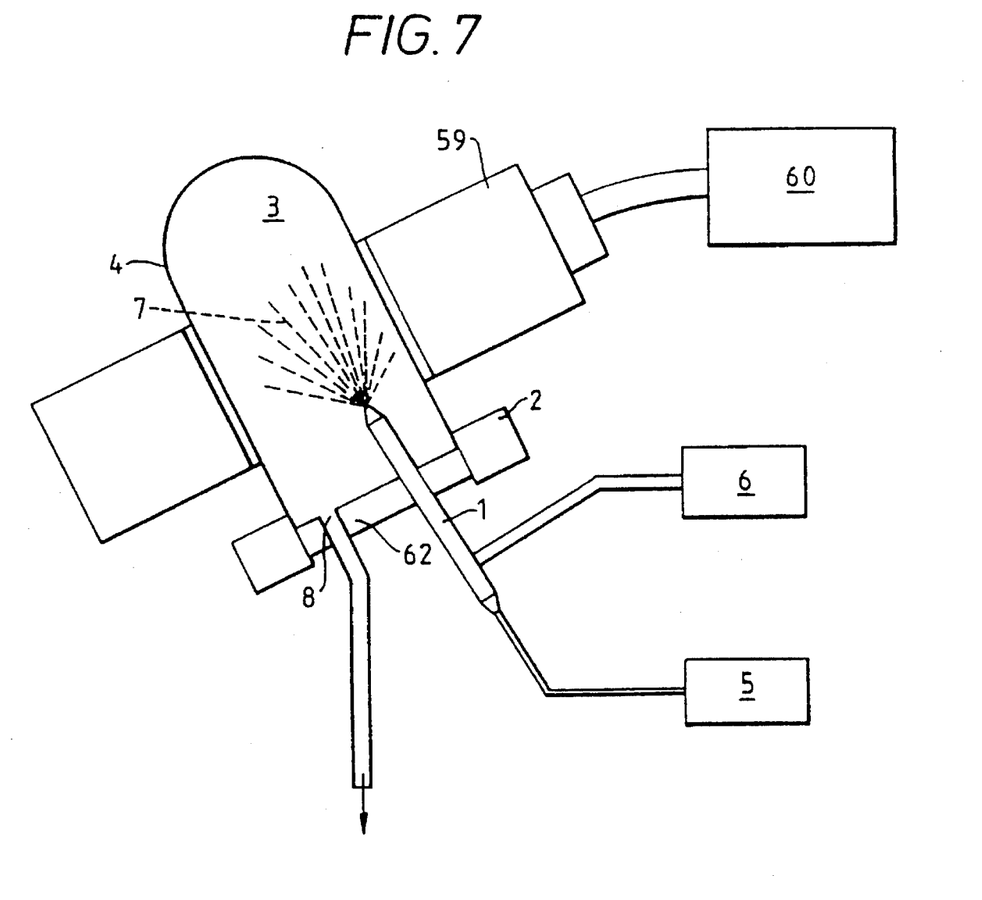
FIG. 7 is a drawing showing how the droplets in the evaporation chamber may be heated by microwave energy.

It is also within the scope of the invention to use microwave energy to heat the aerosol in place of the infra-red radiation employed in the FIG. 2 embodiment. This may be achieved by disposing the evaporation chamber 3 in a microwave cavity 59 which is supplied with microwave power generator 60, as shown in FIG. 7.

We claim:

1. An apparatus for producing an aerosol of desolvated analyte particles comprising nebulizing means for producing droplets of a carrier liquid containing an analyte, evaporation chamber means bounded by a wall for receiving said aerosol, means for subjecting the droplets comprised in said aerosol in said evaporation chamber means to rapid radiative heating to evaporate said carrier liquid from said droplets during their passage through said evaporation chamber means, and cooling means for maintaining the temperature of said wall below the boiling point of said carrier liquid at the pressure inside said evaporation chamber means.

2. An apparatus as claimed in claim 1, wherein the aerosol droplets produced by said nebulizer means have a mean diameter of less than 10 microns.

3. An apparatus as claimed in claim 1, wherein said heating means comprises a heated body disposed outside said evaporation chamber means and the wall of said evaporation chamber means is at least partly transparent to the radiation from said heated body, the temperature and material of said heated body being selected to ensure that the droplets absorb the radiation and become heated.

4. An apparatus as claimed in claim 3, wherein said heating means further comprises a cylindrical elliptical reflector having two foci, said heated body disposed at one of said reflector foci and the other of said foci being located within said evaporation chamber means.

5. An apparatus as claimed in claim 4, wherein the heating means comprises an elongate heating element made of silicon carbide maintained at about 1350° C. by the passage of an electrical current through it.

6. An apparatus as claimed in claim 1, wherein the aerosol droplets are heated by microwave energy.

7. An apparatus as claimed in claim 6, wherein said evaporation chamber means is disposed in a tuned cavity fed from a microwave power generator, and wherein the frequency of operation of said generator is selected to coincide with strong absorption frequencies of the liquid.

8. An apparatus as claimed in claim 1, wherein the power of said radiative heating means is sufficient to evaporate substantially all of the liquid from the droplets during their passage through said evaporation chamber means in less than 50 ms.

9. An apparatus as claimed in claim 1, wherein the aerosol is fed to a plasma torch and wherein said apparatus further comprises condenser means disposed between the aerosol exit of said evaporation chamber means and the plasma torch.

10. An apparatus as claimed in claim 9, wherein a second condenser means of similar construction to the first but maintained at a lower temperature than the first is additionally provided between the exit of the first condenser means and the plasma torch.

11. An apparatus as claimed in claim 1, wherein a filter made of a material having the same or similar absorption characteristics as said chamber wall material is disposed in the path of the radiation from said heating means to said evaporation chamber means.

12. An apparatus as claimed in claim 11, wherein said wall and said filter are comprised of infrared transmissive quartz.

13. An apparatus as claimed in claim 1, wherein the cooling means comprises a fan.

14. An apparatus as claimed in claim 1, wherein the cooling means comprises a water cooled heat sink.

15. An apparatus as claimed in claim 1, wherein said evaporation chamber means comprises a tube having a base and an axis, the axis of said tube being inclined at 20°–30° from the vertical, said base having an aerosol inlet and an outlet, said outlet having a drain.

16. An apparatus as claimed in claim 1, wherein the radiated heat supplied to the droplets is sufficient to cause at least some of the droplets to be physically disrupted into smaller droplets.

17. An apparatus as claimed in claim 16, wherein the smaller droplets produced by said nebulizing means are completely evaporated in said evaporation chamber means.

18. An ICP or MIP optical or mass spectrometer in which the apparatus for producing an aerosol of disolvated analyte is according to claim 1.

19. An apparatus as claimed in claim 1, wherein the aerosol droplets produced by said nebulizing means have a diameter less than 50 microns.

20. An apparatus as claimed in claim 1, wherein the power of the radiative heating means is sufficient to evaporate substantially all of the liquid from the droplets during their passage through said evaporative chamber means in less than 100 ms.

21. A method of producing an aerosol comprising small particles of an analyte in a flow of inert gas for an ICP or MIP torch, the method comprising the steps of:

a) nebulizing a liquid containing said analyte to produce an aerosol comprising droplets of said liquid entrained in said flow of inert gas;

b) passing the droplets into a chamber and rapidly heating the droplets comprising said aerosol by radiant energy to evaporate substantially all the liquid therefrom, thereby producing said aerosol comprising small particles; and c) cooling the walls of the chamber such that the vapour produced by evaporation of said liquid in step b) is condensed and removed from said aerosol.

22. A method as claimed in claim 21, wherein there is provided sufficient heat in step b) for at least some of the droplets present in the aerosol to be disrupted into smaller droplets, each containing a proportion of the analyte originally contained in the droplet prior to its disruption.

23. A method as claimed in claim 21, wherein substantially all of the liquid from the droplets is evaporated in less than 50 ms.

24. A method as claimed in claim 19, wherein the liquid is aqueous and droplets of less than 10 microns in diameter are evaporated to dryness in 10 ms or less.

25. A method of analyzing an analyte in a liquid by ICP or MIP optical or mass spectrometry wherein said liquid is converted to an aerosol by the method of claim 21 and the aerosol so produced is conveyed to the plasma torch of an ICP or MIP spectrometer.

26. A method as claimed in claim 21, wherein substantially all of the liquid from the droplets is evaporated in less than 100 ms.

27. An apparatus for producing an aerosol of desolvated analyte particles comprising nebulizing means for producing droplets of a carrier liquid containing an analyte, evaporation chamber means bounded by a wall for receiving said aerosol, means for subjecting the droplets comprised in said aerosol in said evaporation chamber means, to rapid radiative heating to evaporate substantially all said carrier liquid from said droplets during their passage through said evaporation chamber means, and cooling means for maintaining the temperature of said wall below the boiling point of said carrier liquid at the pressure inside said evaporation chamber means.

28. The apparatus as claimed in claim 27, wherein said heating means provides sufficient heat to disrupt at least some of the droplets present in the aerosol produced by said nebulizing means into smaller droplets, each containing a proportion of the analyte originally contained in the droplet prior to its disruption.

29. The apparatus as claimed in claim 28, wherein the heat supplied by said heating means is sufficient to completely evaporate said smaller droplets produced by disruption before said smaller droplets leave said evaporation chamber means.

30. A method of producing an aerosol comprising small particles of analyte in a flow of inert gas for delivery to an ICP or MIP torch, the method comprising the steps of:

a) nebulizing a liquid containing said analyte to produce an aerosol comprising various size droplets of said liquid entrained in said flow of inert gas;

b) passing said aerosol into a chamber and then rapidly heating said aerosol by radiant energy, said rapid radiant heating causing the disruption of the larger of said droplets formed during the step of nebulizing into smaller droplets and the complete evaporation of said liquid from the remaining of said droplets formed during the step of nebulizing and the smaller droplets resulting from said disruption to thereby produce said aerosol comprising small particles; and c) cooling the walls of the chamber in which the radiant heating occurs to cause vapor produced by the evaporation of the liquid to be condensed and removed from said aerosol.

* * * * *

UNITED STATES PATENT AND TRADEMARK OFFICE
CERTIFICATE OF CORRECTION

PATENT NO. : 5,534,998
DATED : July 9, 1996
INVENTOR(S) : Alan R. Eastgate et al It is certified that error appears in the above-indentified patent and that said Letters Patent is hereby corrected as shown below:

On the title page, delete "[22] Filed: Dec. 14, 1994" and insert in place thereof:

[22] PCT Filed:     Feb. 19, 1993
[86] PCT No.:       PCT/GB93/00355
     §371 Date:     Dec. 14, 1994
     §102(e) Date:  Dec. 14, 1994
[87] PCT Pub. No.:  WO 93/17320
     PCT Pub. Date: Sept. 2, 1993

In column 8, line 36, change "19" to --21--.

Signed and Sealed this

Fifth Day of November, 1996

Attest:

BRUCE LEHMAN

*Attesting Officer*     *Commissioner of Patents and Trademarks*